(12) United States Patent
Li et al.

(10) Patent No.: US 7,252,597 B2
(45) Date of Patent: Aug. 7, 2007

(54) GOLF CLUB ASSEMBLY WITH RECESSED ADJUSTER ASSEMBLY

(75) Inventors: Laurence H. Li, 515 Clark Dr., San Mateo, CA (US) 94402; Jason Tolomeo, San Jose, CA (US)

(73) Assignee: Laurence H. Li, San Mateo, CA (US)

( * ) Notice: Subject to any disclaimer, the term of this patent is extended or adjusted under 35 U.S.C. 154(b) by 0 days.

(21) Appl. No.: 10/208,109

(22) Filed: Jul. 29, 2002

(65) Prior Publication Data

US 2003/0027658 A1 Feb. 6, 2003

Related U.S. Application Data

(63) Continuation-in-part of application No. 09/418,682, filed on Oct. 14, 1999, now abandoned.

(51) Int. Cl.
*A63B 5/06* (2006.01)

(52) U.S. Cl. .................................................. 473/318

(58) Field of Classification Search ............... 473/316, 473/317, 318, 319, 320–323, 282, 289, 219, 473/231, 232, 233, 223, 226, 227, 256, 300, 473/520, 238
See application file for complete search history.

(56) References Cited

U.S. PATENT DOCUMENTS 1,587,918 A 6/1926 Morrison
1,603,904 A 10/1926 Cohn
1,665,195 A 4/1928 Cohn
2,478,131 A 8/1949 Rossi
2,992,828 A 7/1961 Stewart
3,318,602 A 5/1967 Kunihisa
3,833,223 A 9/1974 Shulkin
4,024,666 A * 5/1977 Carver
4,240,631 A 12/1980 MacDougall
4,261,566 A 4/1981 MacDougall
4,685,682 A 8/1987 Isabell
5,226,652 A 7/1993 Sato
5,478,075 A 12/1995 Saia et al.

(Continued)

FOREIGN PATENT DOCUMENTS

EP 0840145 A1 5/1998

(Continued)

OTHER PUBLICATIONS

Summitt, Jeff, *The Modern Guide to Shaft Fitting*, Chapter 1, pp. 4-17.

(Continued)

*Primary Examiner*—William M. Pierce
(74) *Attorney, Agent, or Firm*—Dorsey & Whitney LLP (57) ABSTRACT

A golf shaft having adjustable stiffness and frequency. A hollow golf shaft has a compression assembly disposed along and within the hollow shaft between the butt end and the bend point of the shaft. The compression assembly places the corresponding end of the shaft in compression and permits rapid and easy adjustment of the shaft stiffness and frequency.

14 Claims, 8 Drawing Sheets

U.S. PATENT DOCUMENTS

| | | |
|---|---|---|
| 5,505,446 A | 4/1996 | Whitaker |
| 5,632,693 A | 5/1997 | Painter |
| 5,722,899 A | 3/1998 | Cheng |
| 5,735,752 A | 4/1998 | Antonious |
| 5,935,017 A * | 8/1999 | Weaver et al. ............. 473/319 |
| 6,113,508 A | 9/2000 | Locarno et al. |
| 6,241,623 B1 | 6/2001 | Laibangyang |
| 6,361,451 B1 * | 3/2002 | Masters et al. |

FOREIGN PATENT DOCUMENTS

| | | |
|---|---|---|
| WO | PCT/US99/21928 | 9/1999 |

OTHER PUBLICATIONS

Summitt, Jeff, The Modern Guide to Shaft Fitting, Chapter 6, "A Discussion of Kick Point/Bend Point and Balance Point", pp. 77-92.

* cited by examiner

PIN    KEYWAY    SPLINE

FLATS    SQUARE    HEX

GOLF CLUB ASSEMBLY WITH RECESSED ADJUSTER ASSEMBLY

RELATED APPLICATIONS

This is a continuation-in-part of application Ser. No. 09/418,682 filed Oct. 14, 1999 now abandoned entitled BODY MEMBER WITH ADJUSTABLE STIFFNESS AND FREQUENCY.

FIELD OF THE INVENTION

This invention relates to the field of golf equipment, and more specifically to golf shafts having an adjustable stiffness and frequency.

BACKGROUND

The trend in the golf club industry is towards the construction of customized golf clubs. In customizing a golf club, the physical size of the club should correspond in some way to the size of the golfer. For example, a longer golf club would be suitable for a taller golfer. The weight of the club should also be considered since, in general, a golfer with greater physical strength can swing heavier golf clubs than golfers of lesser strength. These are examples of two factors commonly considered when selecting the proper golf club for a particular individual. Another important parameter to consider is the bending characteristic of the golf club shaft.

Figure 1A:
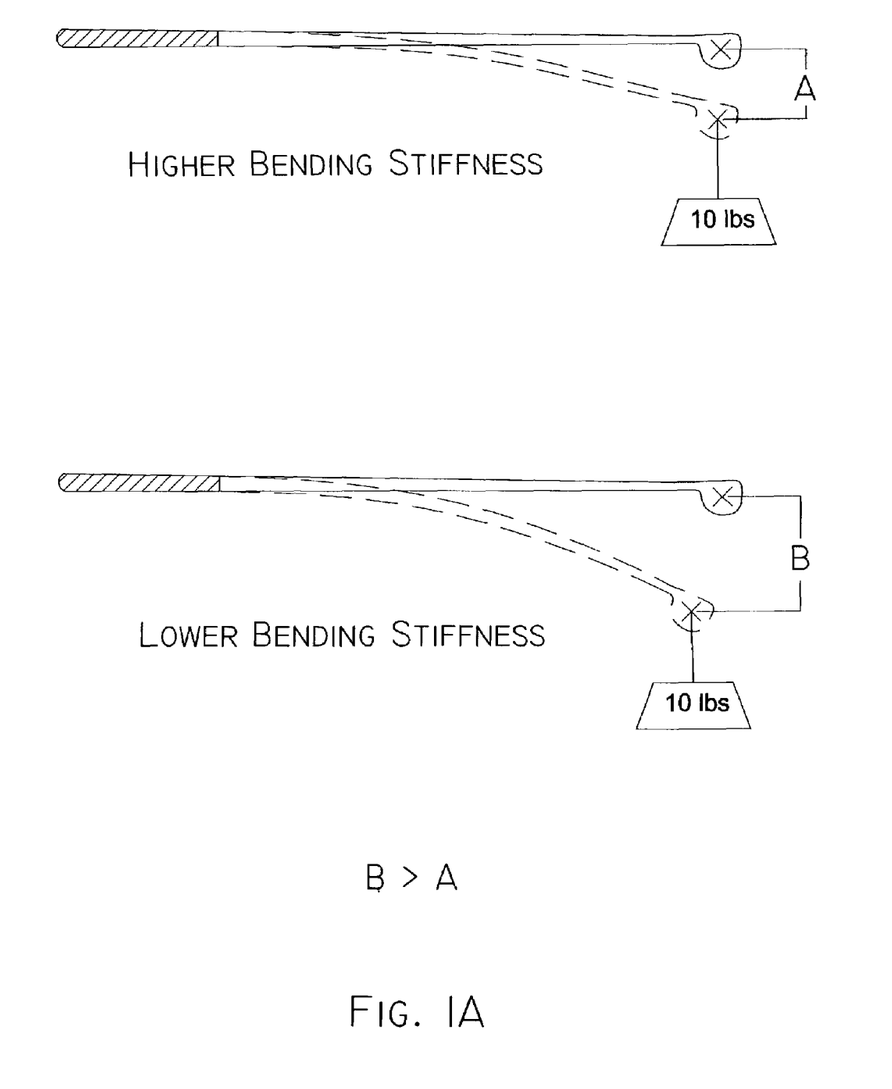
FIG. 1A illustrates the principles of bending stiffness.

The bending of a golf club shaft may be characterized by its bending stiffness and its vibrational bending frequency. The bending stiffness is a measure of how much the golf club shaft will bend (i.e. its displacement) due to an applied force at a specified location on the shaft. If the same force is applied in the same way to two different golf club shafts, the shaft with the smaller displacement is considered to be stiffer, as illustrated in FIGS. 1A.

The vibrational bending frequency of a golf club shaft is the frequency at which the golf club shaft vibrates when bent and then suddenly released, for example, when being held at the grip end and deflected at the head. Such vibration of the shaft is similar to the motion of a car radio antenna when struck. As the shaft vibrates, the number of times the end of the shaft goes back and forth each minute is the vibrational bending frequency measured in cycles per minute.

It is common for golf clubs to be purchased pre-assembled as a set, with the golfer required to adapt to the golf clubs as purchased. Some golf clubs may be selected off-the-shelf with a particular stiffness specification that the golfer deems appropriate for his or her golfing style. Golf club shafts are currently commercially sold in different bending stiffness specifications, examples are: "ladies," "regular," "stiff," and "extra stiff." Each of these specifications relates to a range of bending stiffness values. The exact value of an individual shaft designated with one of the above terms falls somewhere within the range of values described by that specification. The purpose of these various shaft bending stiffnesses is to allow the custom assembly of a golf club with a vibrational bending frequency that best compliments a golfer's particular strength and swing speed One problem with selecting golf clubs with a fixed bending stiffness and vibrational bending frequency is that it is rare for a golfer's swing tempo to precisely match with an off-the-shelf set of clubs. Another problem is that it is also rare for a set of clubs to have physical parameters such as bending stiffness, mass and vibrational bending frequency consistent between each club within a set.

One solution is to provide a custom-made set of clubs where a golf professional or person with technical expertise consults with the golfer prior to the assembly of the golf club. The consultant chooses the golf club shaft bending stiffness, length and head weight to best suit the individual golfer.

A problem with providing a custom set of clubs is that commonly only a range of discrete vibrational bending frequencies are attainable. Furthermore, the range of discrete vibrational bending frequencies may not be available at all for certain combinations of shaft length and head weight. In addition, once the club is assembled, the vibrational bending frequency and shaft bending stiffness cannot be easily changed without re-manufacturing the golf club.

Some prior golf club shafts are designed to provide very specific shaft bending stiffnesses at different locations along the shaft's length. One prior golf club shaft uses an interior bar within a hollow shaft, and a number of coupling inserts to alter shaft stiffness. When engaged, the coupling inserts attach the shaft to the interior bar, thus increasing the overall stiffness of the club. A problem with such a shaft is that it may provide only minimal stiffness increase due to the inefficient location of the central bar and its contribution to the overall bending moment of inertia. Further, the mass increase of such a device on the overall club mass may be substantial in relation to the stiffness change provided. Such added weight may not be desirable with certain golfers.

Another problem with some prior golf club shafts is that their stiffness may not be altered after they have been assembled by the manufacturer. A golfer's skill level and preferences may change over time and, thereby, the golfer may desire a different stiffness to his clubs. As such, the golfer may be compelled to purchase a new set of clubs or to disassemble and reassemble his/her clubs using new components.

One prior golf club design provides the capability of changing the shaft stiffness of a golf club after it has been assembled. The golf club's stiffness may be changed by pressurizing the shaft with air. One drawback of such a device is that the use of pressure levels necessary to achieve a real benefit may create significant safety issues.

As such, these prior golf clubs do not provide the individual golfer with the capability of changing the bending stiffness and the vibrational bending frequency of a given set of clubs after the clubs have been assembled and purchased without substantially changing the mass of the club or introducing significant safety issues.

SUMMARY OF THE INVENTION

The present invention pertains to an apparatus for force adjustment within a golf shaft. The apparatus includes a golf shaft and a load member disposed within the shaft to generate a force on the shaft. The apparatus may also include an adjuster coupled to the load member to adjust the force on the golf shaft.

Additional features and advantages of the present invention will be apparent from the accompanying drawings and from the detailed description that follows.

BRIEF DESCRIPTION OF THE DRAWINGS

The present invention is illustrated by way of example, and not by way of limitation, in the figures of the accompanying drawings in which.

DETAILED DESCRIPTION

In the following description, numerous specific details are set forth, such as examples of specific materials, mechanisms, dimensions, etc., in order to provide a thorough understanding of the present invention. It will be apparent, however, to one skilled in the art that these specific details need not be employed to practice the present invention. In other instances, well known materials or methods have not been described in detail in order to avoid unnecessarily obscuring the present invention.

An apparatus for force tuning within a golf shaft is described herein. In one embodiment, the apparatus includes a tapered golf shaft having a bending stiffness and a vibrational bending frequency. A load member is coupled to the tapered golf shaft. The load member allows for the bending stiffness and the vibrational bending frequency to be altered. Such alteration may occur after the apparatus is assembled.

The method and apparatus described herein is preferably implemented with a golf club as discussed in detail below. Although the method and apparatus are described in relation to a golf club, this is only for illustrative purposes and is not meant to be limited to use in a golf club but can also be used with other devices having tapered shafts.

Figure 1B:
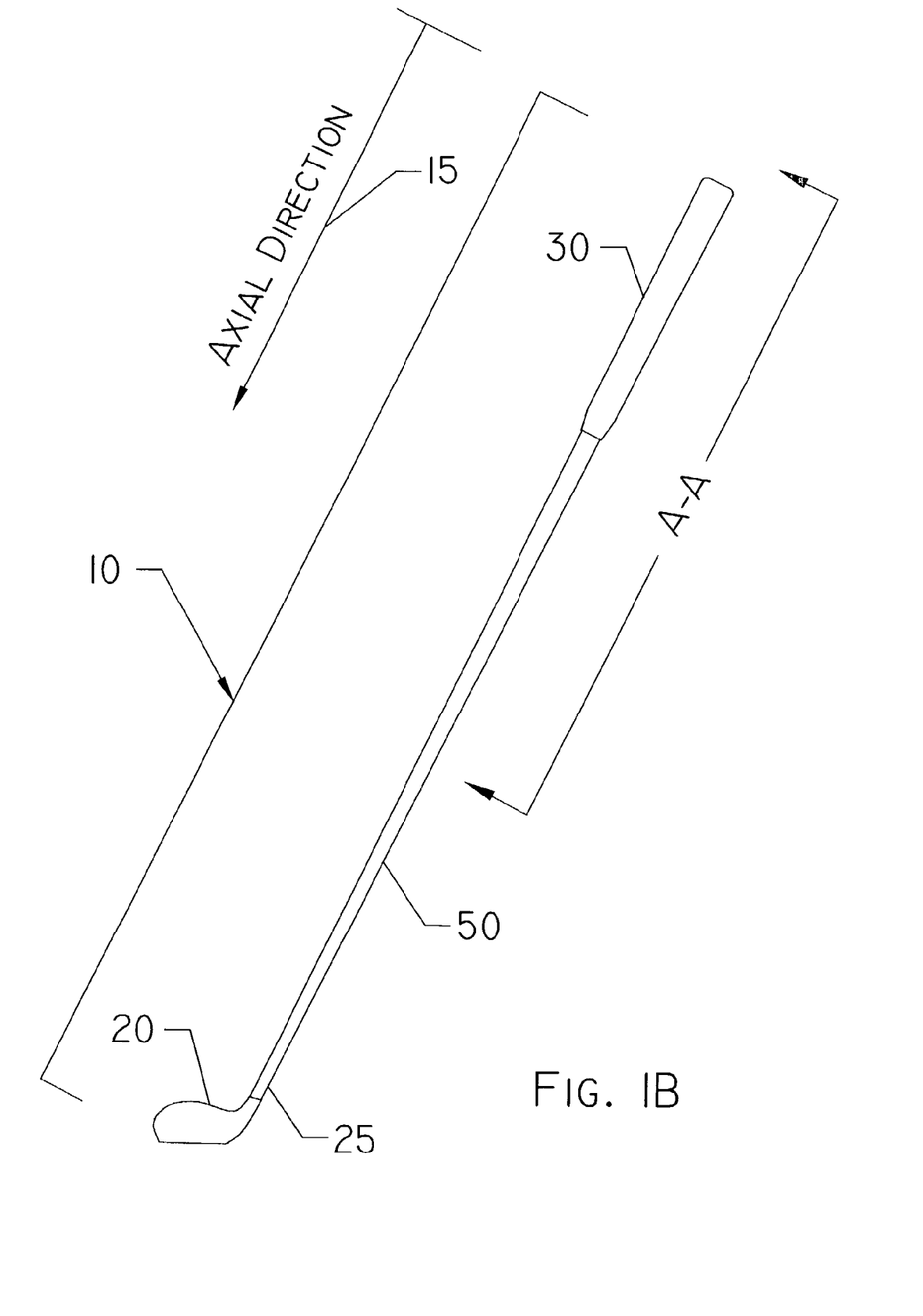
FIG. 1B illustrates one embodiment of a golf club having a force tuning device.

FIG. 1B illustrates one embodiment of a golf club having a force tuning device. Golf club 10 includes a head 20 and a tapered shaft 50. The shaft 50 has a head or tip end 25 and a handle or butt end 30. Head end 25 may be coupled to head 20. In one embodiment, handle end 30 is an area of golf shaft 50 by which a user typically holds a golf club 10. The handle end 30 may be wrapped in a material suitable for gripping by the user. In another embodiment, handle end 30 may be coupled to a separate handle piece. The axial direction 15 is along the length of golf club 10.

The performance of golf club 10 may be characterized by parameters such as its bending stiffness and its vibrational bending frequency. The bending stiffness of shaft 50 is a measure of how much the shaft will bend due to an applied force at a specified location. The vibrational bending frequency of shaft 50 is the frequency at which shaft 50 vibrates when bent and then suddenly released, for example, when being held at handle 30 and deflected at head 20. As tapered shaft 50 vibrates, the number of times that head end 25 moves back and forth, per a unit of time period, is its vibrational bending frequency.

The vibrational bending frequency depends on the bending stiffness of the shaft 50, as well as the mass of the shaft 50 and head 20. If shaft 50 is made stiffer, with the mass of shaft 50 and head 20 constant, the vibrational bending frequency increases. Conversely, if the mass of shaft 50 or head 20 is increased, with the bending stiffness of shaft 50 remaining constant, the vibrational bending frequency decreases. Thus, the vibrational bending frequency of golf club 10 may be changed by altering its mass and/or its bending stiffness. Golf club 10 includes a device within the shaft 50 for adjusting a force on the butt end portion A-A of shaft 50 that is proportional to the change in bending stiffness and the change in the square of the vibrational bending frequency of golf club 10.

Referring to FIG. 1A, it is observed that a significant portion of the displacement of the head of the golf club is attributable to bending associated with the handle or butt end of the tapered shaft. Thus, we have found that the force tuning device should be in the upper or butt end of the shaft for control of stiffness without affecting the other shaft characteristics. More particularly, we have found that the inner insert should be located within a designated range of distance from the butt and no further along the shaft than the bend point. The bend point is defined in the Dynacraft publication entitled, "The Modern Guide to Shaft Fitting," as follows:

> Bend point is determined through a mechanical test, which compresses one end of the shaft toward the other to create a curve. Either through a predetermined amount of compressive force or by dictating how much of a curve must be achieved through the application of force, the position on the shaft that deviates the furthest from the shaft's original center line is defined as the bend point.

In order to find the bend point, it should be understood that the shaft is caused to bend by initiating the bending with a small sideways force applied at a point along the middle of the shaft, otherwise the shaft would be put into a purely axial load condition resulting in compression of the shaft with no bending.

The inner insert should not be installed beyond the bend point of the shaft. This avoids changing the characteristics of the shaft that affect the launch angle and feel of the shaft. The proximal location limit of the inner insert is 25% down from the butt of the shaft. This is dictated by load and stress consideration. Having the inner insert located 25% in from the butt requires more than four times the load necessary for the same range of adjustment as an inner insert located at or near the bend point. The larger loads necessary to produce the reduction in bending stiffness requires larger inserts in order to be able to support the increase in forces. This causes the weight of the device to increase. Interlaminar failures of composite shafts are a possibility when stresses rise too high. Also, the bend contour of the shaft must be considered. By locating the inner insert too close to the butt, the shaft may appear "lumpy" or discontinuous when bending. We have found that the load member is preferably between the butt and the bend point, which is generally between one-fourth and one-half the length of the shaft in from the tip.

Figure 2:
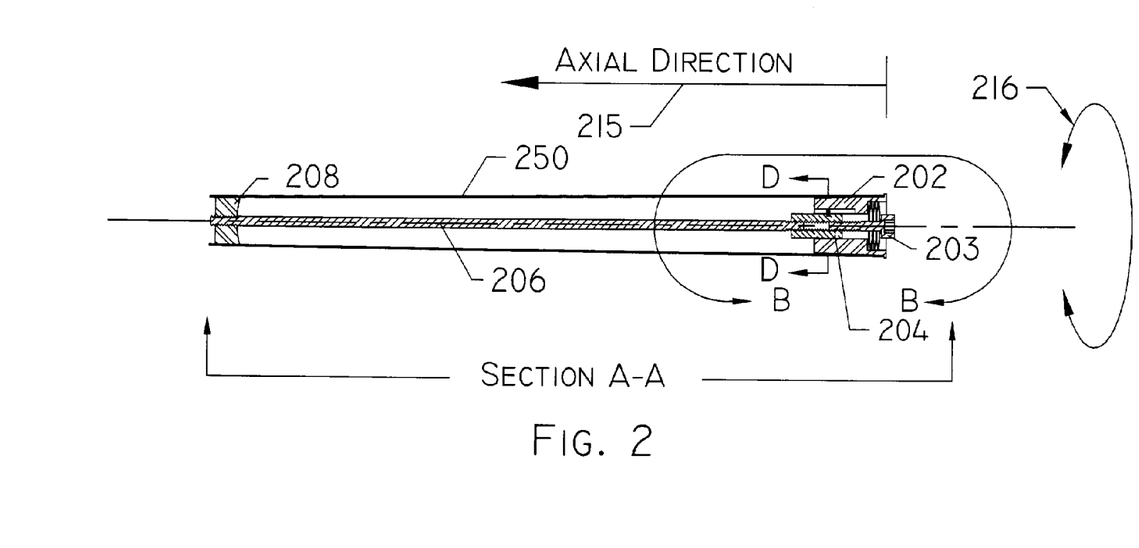
FIG. 2 illustrates a cut through view of one embodiment of a golf shaft.

FIG. 2 illustrates a cut through view of the butt end of a tapered shaft. The section A-A of FIG. 2 corresponds to the butt end of section A-A of FIG. 1B. The hollow shaft has a circular cross sectional structure and contains the mechanism for adjusting the stiffness and frequency of the shaft.

In one embodiment, the butt end of the hollow tapered shaft includes inner insert 208 and outer insert 202. The size and diameter of inserts 202 and 208 may be designed to provide coupling within shaft 250 at a desired location along the hollow shaft. Inserts 202 and 208 are positioned within shaft 250 along the region where stiffness of the shaft is to be adjusted. In one embodiment, outer insert 202 may be coupled to the shaft 250 at the butt and inner insert 208 may be coupled to shaft 250 at the approximate center or bend point of the shaft. In an alternative embodiment, the outer insert may be coupled at other positions within the end of the shaft. The insertion depth of the inner insert should be above the bend point of the shaft so as to avoid changing the general playing characteristics of the shaft other than flex, i.e. the golf industry currently feels that the location of the bend point, and the stiffness of the shaft tip, affects the trajectory of the ball and the feel of the club.

In one embodiment, inserts 202 and 208 may be coupled to shaft 250 by bonding. In an alternative embodiment, inserts 202 and 208 may be constrained within shaft 250 by other methods, for example, integrally manufactured into shaft 250. Such methods are well known in the art; accordingly, a more detailed description is not provided herein.

A load member 206 extends between inserts 202 and 208. Load member 206 may be coupled to inner insert 208 at one end. The other end of load member 206 may be coupled to outer insert 202. In one embodiment, load member 206 carries a tension load between the inserts 202 and 208 so that the section of shaft 250 between inserts 202 and 208 may be subjected to compression along its axial direction 215. The load member extends along the central or neutral axis of the shaft spaced from the walls. Once the shaft is loaded and bent, if the load member does not touch the wall of the shaft, the force within the load member is purely axial. If, however, the load member contacts the side of the shaft, the segment in contact is subjected to a combination of side and axial forces. The side force on the load member is created by the wall of the shaft. There is an equal and opposite force acting on the wall of the shaft thereby forcing the shaft to straighten. This is avoided by locating the inner insert as described above.

In one embodiment, load member 206 is a rod. In alternative embodiments, load member 206 may be another type of elongated structural member capable of carrying a tension force along axial direction 215 of shaft 250, for example, a tube or a cable. Load member 206 may be constructed of a tension retaining material that does not exhibit significant time degradation or creep that would lessen the amount of force carried. Creep refers to the property of a material whereby the physical dimension of the loaded part changes as a function of time as well as load. Steel, aluminum, titanium, invar, carbon fiber composites and boron fiber composites are examples of such materials that are highly resistant to creep. In an alternative embodiment, load member 206 may be configured to carry a compressive load.

The inserts and the load member are not limited only to the configuration illustrated in FIG. 2. As previously discussed in an alternative embodiment, the inserts 202 and 208 may be located along the shaft at different locations in order to target the stiffness along prescribed regions of its length.

Referring again to FIG. 2, in one embodiment a load adjuster 203 is coupled to load member 206 via coupler 204. Tuning of the bending stiffness and vibrational bending frequency of shaft 250 may be performed at any time through use of load adjuster 203. In one embodiment, the tuning may be performed by turning load adjuster 203 in a rotational direction 216. Rotating load adjuster 203 produces a tension force in load member 206 and an opposite compression force on the shaft 250, as illustrated in FIG. 3.

Figure 3:
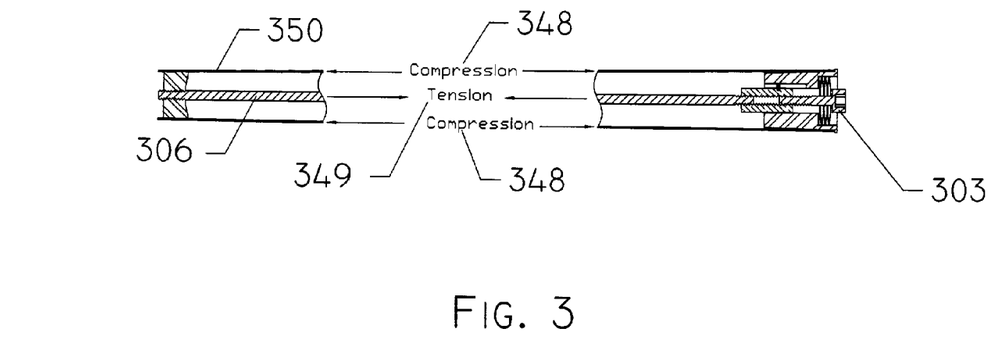
FIG. 3 illustrates one embodiment of the internal forces within a golf shaft.

FIG. 3 illustrates one embodiment of the internal forces within a shaft. Changes in the bending stiffness and vibrational bending frequency of shaft 350 is related to the axial force applied to it. A force 348, that is, a compression load, in shaft 350 causes a decrease in its bending stiffness and a corresponding decrease in its vibrational bending frequency. Conversely, a reduction in the compressive force 348 in the shaft 350 causes a corresponding increase in the vibrational bending frequency, up to the properties of a shaft without the tensioning member 306 installed. As such, a user may reversibly and repeatably tune shaft 350 to a desired frequency by moving load adjuster 303. Because the internal forces are applied at the butt end, the bending stiffness and corresponding decrease in vibrational bending frequency of the tapered shaft is achieved without changing other shaft properties such as bend point or tip flex.

The internal force 349 on the load member 306 is described as being a tension load, and the internal force 348 on shaft 350 as being a compressive load. The description would also be applicable if the internal force 349 on the load member 306 were described as a compressive load and the corresponding internal force 348 on the shaft 350 as being a tension load. In this embodiment, the change in bending stiffness and vibrational bending frequency of the shaft 350 increases as the compressive internal force in the load member was increased. As such, the force on the load members in the figures (e.g. load member 206 of FIG. 2 and 406 of FIG. 4) may be described as a tension load and the force on the shafts of the figures (e.g. shaft 250 of FIG. 2 and 450 of FIG. 4) may be described as a compression load. In an alternative embodiment, the force on the load members in the figures may be a compression load and the force on the shaft may be a tension load.

A golfer may quickly tune the golf club to a preferred setting by turning load adjuster 303 to try the golf club at various vibrational bending frequencies. In another embodiment, the vibrational bending frequency of a golf club having shaft 350 may be measured quantitatively and correlated to a calibration scale on the shaft. This provides an indicator by which a golfer can visually adjust the parameters of the shaft to a given setting.

Figure 4:
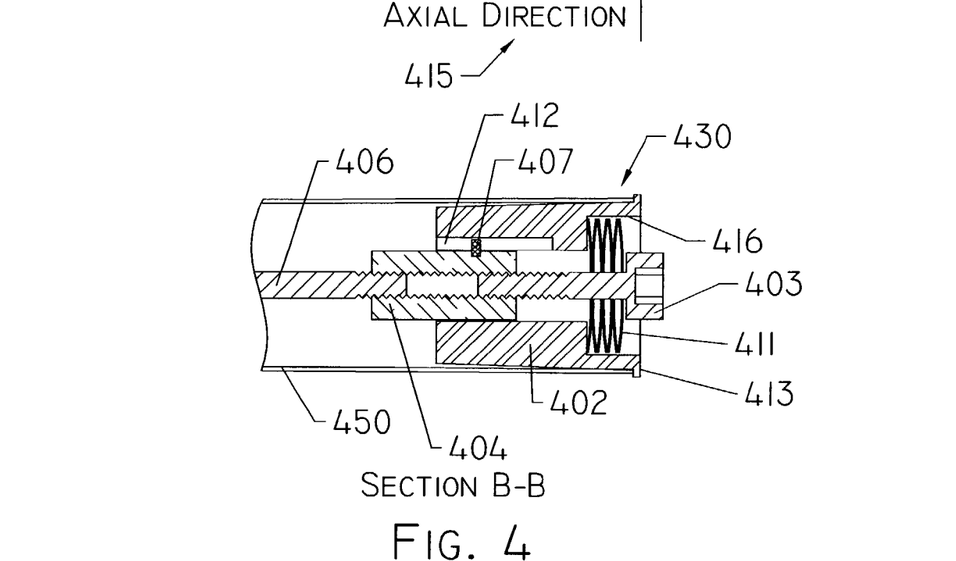
FIG. 4 illustrates one embodiment of an adjuster for adjusting the bending stiffness and vibrational bending frequency of a golf shaft.

FIG. 4 illustrates one embodiment of an adjuster for a force tuning device. In one embodiment, outer insert 402 is disposed within end 430 of shaft 450. One end of insert 402 has a lip 413 that transitions to a larger diameter than shaft 450. The edge of lip 413 seats insert 402 against shaft 450 when installed, and prevents insert 402 from dropping into the cavity of shaft 450. As such, insert 402 provides a firm attachment point to body 450 for additional components.

In one embodiment, load member 406 is attached to a coupler 404 that may be placed in insert 402. Load adjuster 403 is attached to coupler 404 from a side opposite that of load member 406. Load member 406 extends between insert 402 and another insert (not shown) within shaft 450. Load member 406 carries a tension load so that the section of shaft 450 between the inserts places that section into axial compression.

In one embodiment, coupler 404 has a coupler key 407 that fits into keyway slot 412. Keyway slot 412 allows coupler 404 and load member 406 to move along the axial direction 415 of shaft 450, within insert 402. Keyway slot 412 also prevents relative rotation between coupler 404 and insert 402 about the axial direction 415 of shaft 450.

Figure 5A:
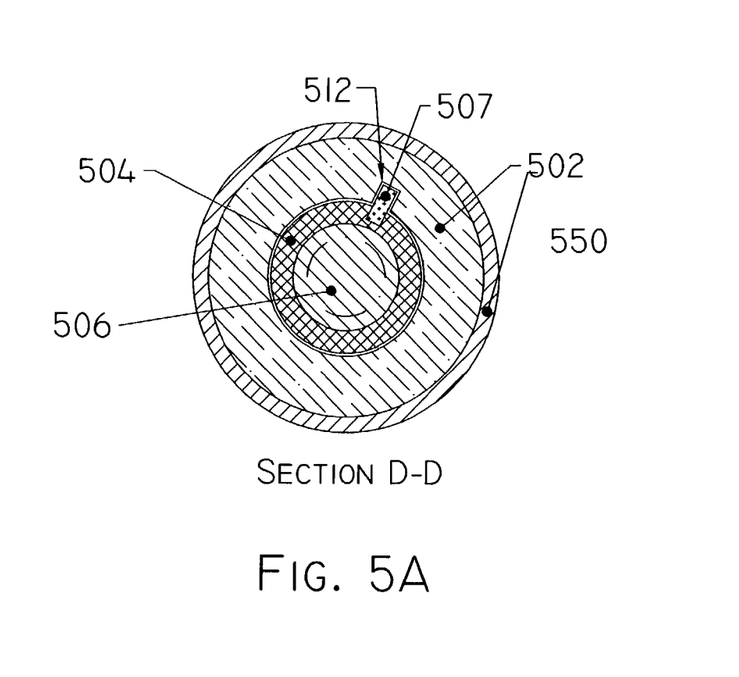
FIG. 5A illustrates a cross section of one embodiment of a golf shaft.
Figure 5B:
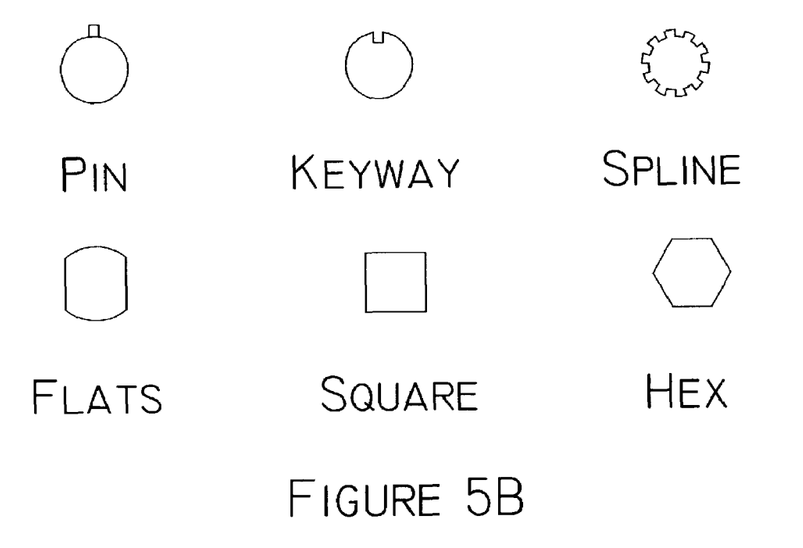
FIG. 5B illustrates cross sections of alternative embodiments of a coupler.

FIG. 5A illustrates a cross section of one embodiment of a shaft. Load member 506 is attached to coupler 504 that is inserted into insert 502. In one embodiment, coupler 504 has a non-circular cross-section such that a pin 507 resides at one point along its circumference. Insert 502 has a correspondingly sized keyway 512 disposed within it that will accept pin 507. Keyway 512 prevents the rotation of coupler 504 when the load adjuster (e.g. load adjuster 403 of FIG. 4) is turned. This forces coupler 504 to slide up and down within insert 502 (i.e. into and out of the page) in response to the amount of tension being applied by the load adjuster (not shown). In another embodiment, coupler 504 may be formed as an integral part of load member 506. In alternative embodiments, coupler 504 may have other configurations to allow for axial motion of load member 506 (into and out of the page) while preventing rotation, for example, a spline, a flat, a square and a hex, as illustrated in FIG. 5B.

Referring again to FIG. 4, coupler 404 is coupled to load adjuster 403. In one embodiment, coupler 404 may be a screw mechanism. Coupler 404 may have male or female threads where it attaches to load adjuster 403. Turning load adjuster 403 in one direction causes coupler 403 to bring load member 406 and load adjuster 403 closer together. This movement produces a tension force in load member 406 and an opposite compression force in shaft 450, similar to that discussed above in relation to FIG. 3.

Figure 5C:
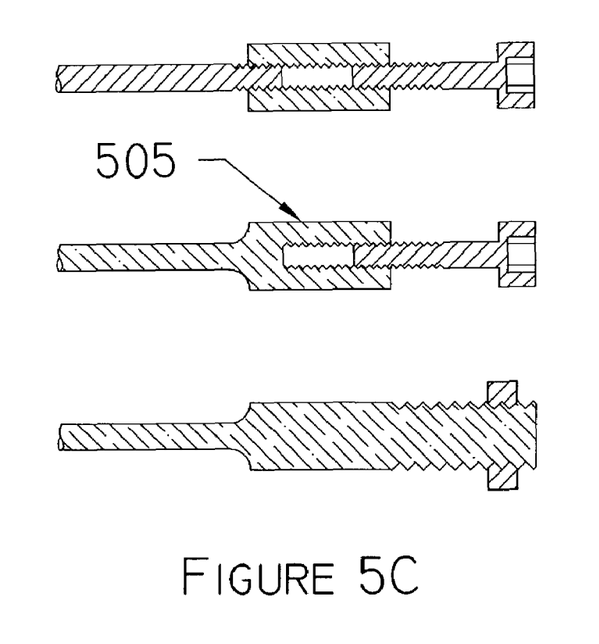
FIG. 5C illustrates alternative embodiments of a screw mechanism.

Various configurations of a screw mechanism are illustrated in FIG. 5C. For example, the load member and coupler may be integrated into one component 505 of FIG. 5C. In an alternate embodiment, adjuster 403 may be another type of mechanism for providing an axial load to load member 406, for example, a cam mechanism. Screw and cam mechanisms are well known in the art; accordingly, a more detailed description of their operation is not provided herein.

As such, the tuning of the bending stiffness and the vibrational bending frequency of shaft 450 may be performed by adjusting load adjuster 403. In addition, this tuning procedure may be performed at any time after the assembly of the components within shaft 450. The use of a linear screw mechanism enables the bending stiffness and vibrational bending frequency to be adjusted over a continuous range of values, rather than just a few discrete values. In an alternative embodiment, a non-linear mechanism may be used to provide adjustment in a discrete range of values, for example, a ratchet mechanism.

In one embodiment, spring 411 may be positioned between load adjuster 403 and insert 402 to provide approximately a constant tension in shaft 450, regardless of the amount of bending deflection of shaft 450. In one embodiment, spring 411 may be belleville springs for compactness, as shown in FIG. 4. In alternative embodiments, spring 411 may have other designs, for example, it may be a compressive or extensive coil spring. Spring 411 may be soft enough so that it would provide a relatively large ratio in the adjustment of load adjuster 403 to the force transmitted to load member 406. As such, changes in the force that produces tension on load member 406 may be easily controlled with broad tolerance on the adjustment requirement of load adjuster 403. This increases the robustness of the design.

Without spring 411, very small changes in adjustment of load adjuster 403 may create very large tension forces if load member 406 is relatively stiff. In another embodiment, the selection of a sufficiently compliant load member 406 may reduce or eliminate the need for spring 411. Spring mechanisms are well known in the art; accordingly, a more detailed description of their operation is not provided herein.

A calibrated scale 416 may be used to provide a visual indication of the stiffness and frequency setting. In one embodiment, calibrated scale 416 may be etched on the inner surface of insert 402 and viewed as load adjuster 403 is adjusted. In alternative embodiments, calibrated scale 416 may be positioned at other locations to allow for a user to visually inspect the scale. For example, calibrated scale 416 may be positioned on the outside surface of shaft 450, with a window slot cut in shaft 450 and insert 402 such that the position of load adjuster 403 may be visible from the exterior of shaft 450.

Figure 6:
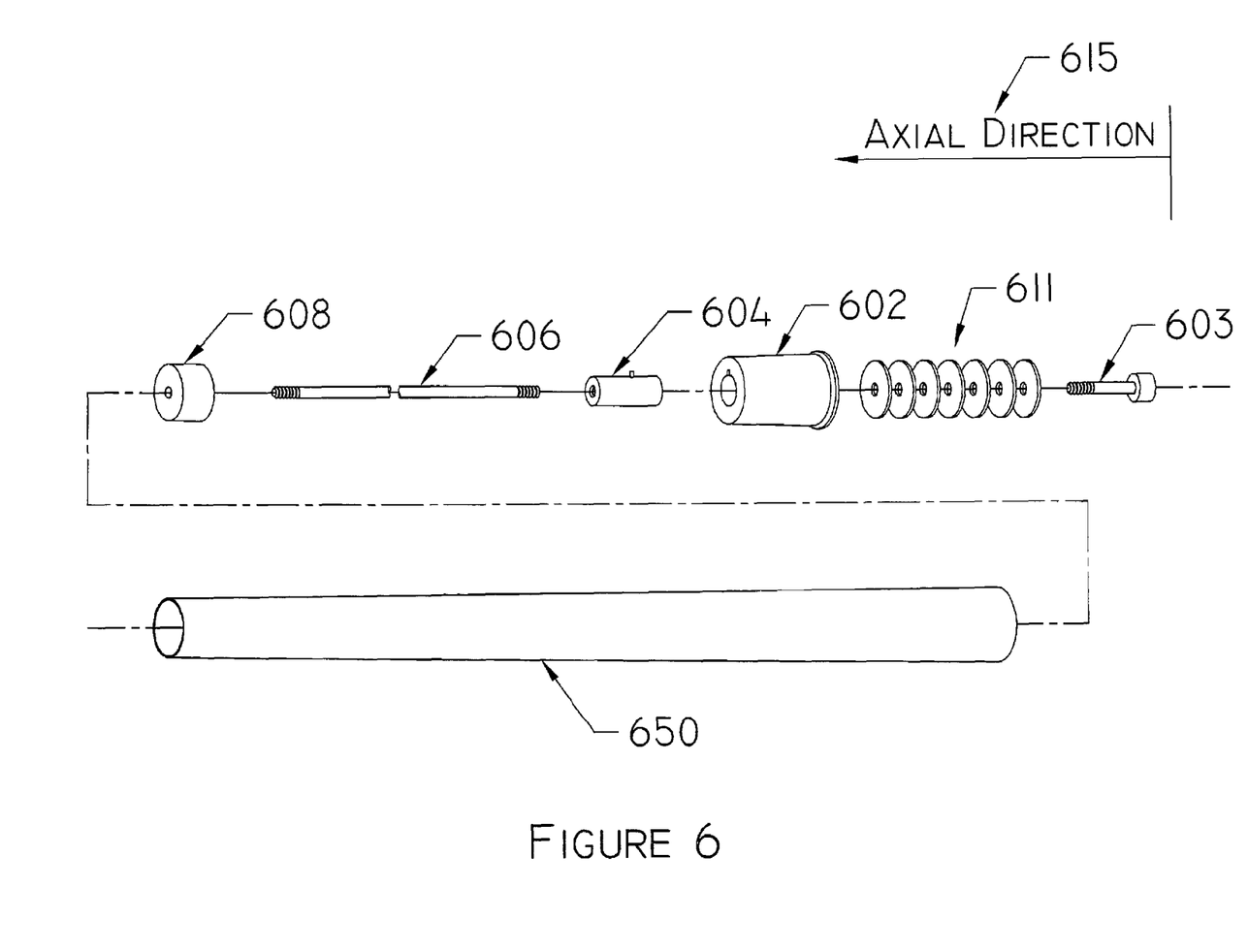
FIG. 6 illustrates an exploded view of one embodiment of a force tuning device contained within a golf shaft.

FIG. 6 illustrates an exploded view of one embodiment of a stiffness and frequency tuning device within a shaft. In one embodiment, insert 608, load member 606, coupler 604, insert 602, spring 611 and load adjuster 603 may be assembled independent of shaft 650. The assembled components may then be slid into shaft 650 having a bonding agent pre-applied in appropriate locations to bond the inserts. In one embodiment, insert 608 may be installed in shaft 650 by bonding insert 608 with a high strength adhesive such as an epoxy. In another embodiment, insert 608 may be coupled to shaft 650 by other methods, for example, by integrally forming the insert into the shaft.

Figure 7:
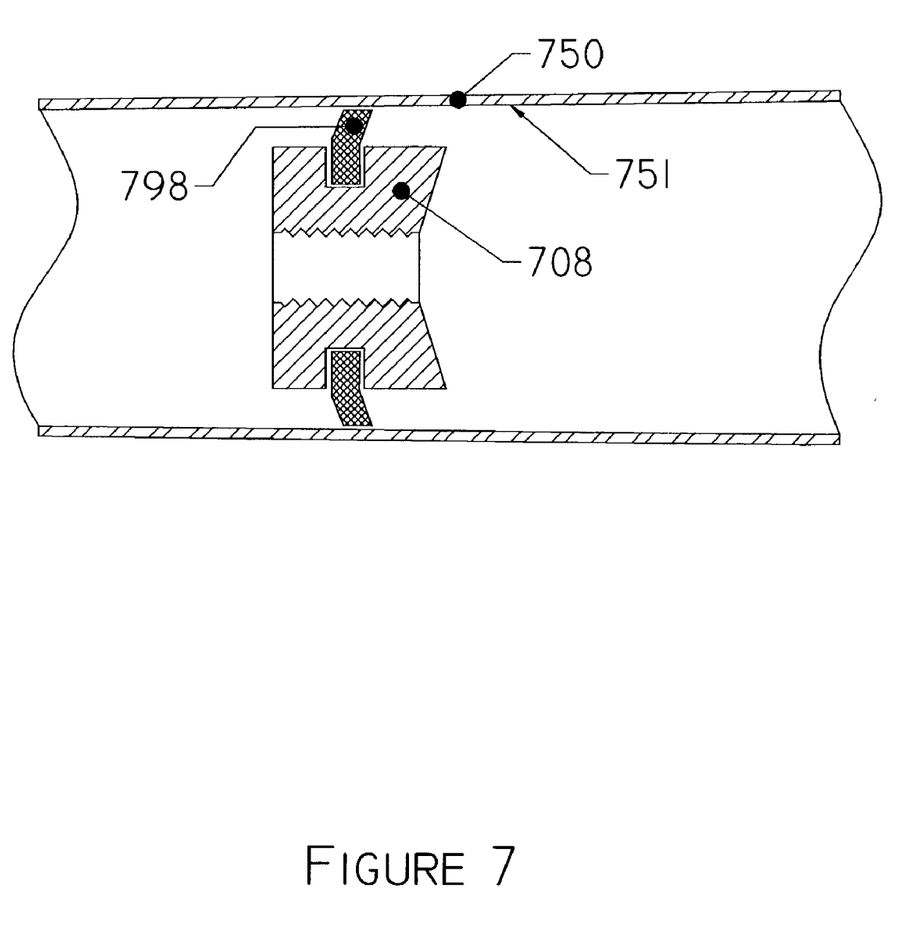
FIG. 7 illustrates an alternative embodiment of insert assembly in a golf shaft.

FIG. 7 illustrates an alternative embodiment of an insert assembly in a shaft. Insert 708 may be a self-locking insert having gripping teeth 798 disposed around its outer surface. Self-locking insert 708 may be pressed into shaft 750 until gripping teeth 798 bite into the inner surface 751 of shaft 750. By using a self-locking insert, a bonding agent may not be necessary to anchor insert 708 into shaft 750. In another embodiment, self-locking insert 708 may have other configurations, for example, the self-locking insert may be threaded to accept a load member, have a hole to accept a load member anchored by some other means, or be integrally attached to the load member.

Figure 8:
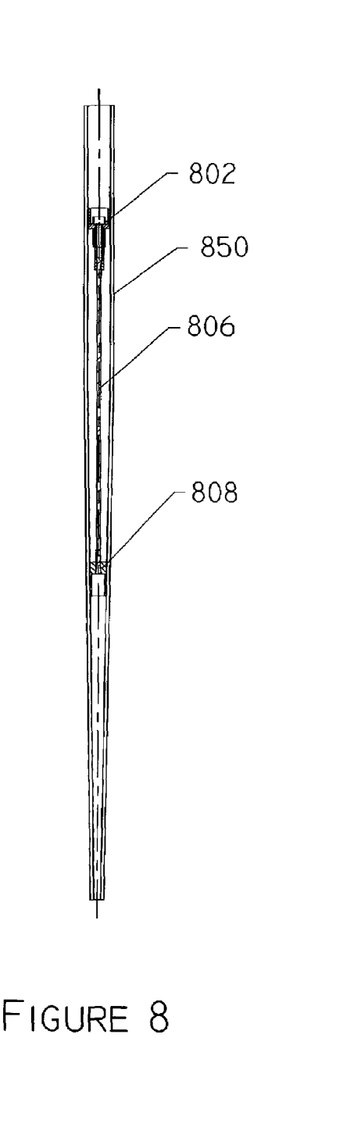
FIG. 8 illustrates a cut through view of an untrimmed golf club.
Figure 9:
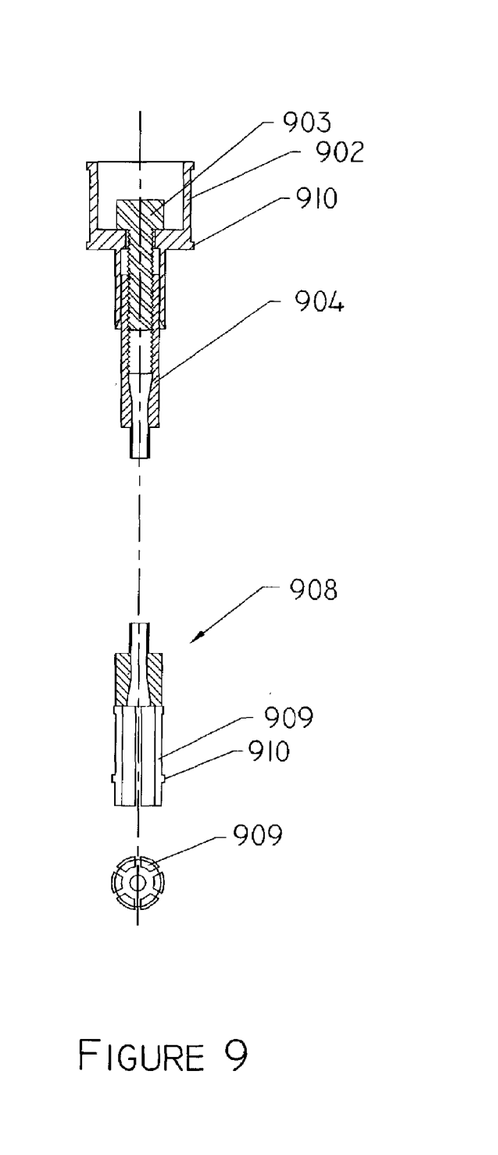
FIG. 9 illustrates another embodiment of an adjuster for adjusting the bending frequency of a golf club, and a diameter compensating inner insert.

The installation methods illustrated in FIGS. 6 and 7 may be performed on readily available shafts without the need to alter the shaft other than by attaching the force tuning device In the foregoing embodiments, it was assumed that the hollow tapered shaft had been trimmed to the final length before the adjustment assembly was mounted. In production, this may not be practical. FIG. 8 shows an embodiment where the outer insert 802 is installed a suitable distance in from the butt of the uncut shaft. This would allow the club assembler the ability to tip and butt trim the shaft to fit the particular club. Contrary to the current reason for tip and butt trimming, which is to select the proper portion of the raw shaft in order to achieve a desired flex, the purpose of tip trimming in this embodiment would be to position the bend point a select distance from the head and then allow the butt to be trimmed to the final desired club length. The inserted distance will depend upon each particular beginning shaft length. It should be such as to allow the assembler to trim the butt end of the shaft. This embodiment enables the clubmaker to assemble the golf club using exactly the same techniques that are currently employed, with the exception that final shaft stiffness is adjustable therefore simplifying the selection of the proper shaft flex for the particular golf club. This attribute makes this golf club shaft a direct replacement of the shafts currently used. A hollow tapered shaft is shown in FIG. 8 with a tensioning assembly including an inner insert 808 and an outer insert 802 inserted inward from the butt of the shaft. The outer insert and inner inserts are suitably secured to the interior of the shaft as described above. The outer coupler includes a screw 903, FIG. 9, that engages a coupler 904 to tension the load member 806 which is secured to the inner insert. The inner insert is positioned in the vicinity of the bend point region. The one piece inner insert 908 incorporates flexible fingers 909 that bend inward as the inner insert is pushed further down a tapered shaft in order to accommodate the smaller diameter toward the head end of the golf club. Ridges 910 are located at various points along the inner insert in order to ensure a consistent bond line around the circumference of the insert. These ridges can be circumferential or longitudinal or they could even be bumps. As an alternate embodiment, indentations could be placed on the surface of the inner insert in order to accept the bonding agent. These ridges 910 are also incorporated in the outer insert 902.

Another benefit of recessing the outer insert is that the added weight is located closer to the head thereby reducing the feeling of "backweighting." Backweight is the idea of reducing the "head heavy" feeling of the club. Backweighting is undesirable in modern clubs, at least among many current manufacturers that are marketing clubs with extreme head heavy swingweights under the assumption that the more weight you can move to the head, the more powerful will be the impact. This philosophy is not embraced by all golfers, one such golfer being Jack Nicklaus, who always backweighted his clubs.

The manufacturing process described above may be used to replace the current practice of manufacturing several different shaft stiffness types and, thus, may reduce tooling and assembly costs for manufacturers. In addition, the use of an adjustable stiffness and frequency shaft may reduce the inventory of wholesalers and retailers who currently have to carry several shafts with different stiffness specifications to accommodate various users.

Furthermore, when used within a set of shafts, the apparatus described herein may be used to match the frequency between individual shafts so that the entire set may be tuned to a similar desired frequency. In addition, the stiffness and frequency tuning may be accomplished after the set of shafts has been assembled, without strict regard to their initial frequency values.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed:

1. A golf club assembly comprising:
   an elongate hollow shaft tapering from an opened first end to a second end and having a neutral axis of bending located along a center line of the hollow shaft wherein the hollow shaft includes a handle portion located at the first end for a user to grip and a bend point along the shaft and tip flex at the portion of the hollow shaft adjacent the second end;
   an insert secured within the hollow shaft only between the first end and the bend point of the shaft so that the hollow shaft is free of the insert between the bend point and the second end,
   a load member disposed within the hollow shaft along the neutral axis with a first end portion coupled to the insert; and
   an adjuster assembly coupled between the hollow shaft and a second end portion of the load member for tensioning the load member so as to adjust the bending stiffness of the hollow shaft between the insert and the adjuster assembly, the adjuster assembly being disposed entirely within and spaced a distance inwardly in an axial direction from the first end of the hollow shaft toward the second end for facilitating trimming of the first end of the hollow shaft.

2. The golf club assembly of claim 1, further comprising a golf club head mounted at the second end of the hollow shaft.

3. The golf club assembly of claim 1, wherein the adjuster assembly includes means for adjusting the compression of the shaft over a continuous range of compressive values.

4. The golf club assembly of claim 3, wherein the adjuster assembly is configured to linearly adjust the tension of the load member.

5. The golf club assembly of claim 4, wherein the adjuster assembly includes a screw mechanism.

6. The golf club assembly of claim 1, further comprising a spring coupled between the adjuster assembly and the load member to provide a substantially constant load throughout the range of bending of the hollow shaft.

7. The golf club assembly of claim 1, wherein the load member is a rod.

8. The golf club assembly of claims 1 or 7, wherein the load member is creep resistant.

9. The golf club assembly of claims 1 or 3, wherein the adjuster assembly includes an adjuster insert coupled to the hollow shaft and a load adjuster acting between the adjuster insert and the first end portion of the load member.

10. The golf club assembly of claim 1, wherein the insert is integral with the hollow shaft.

11. The golf club assembly of claim 1, wherein the insert locks to the interior of the hollow shaft.

12. A golf club assembly comprising:
    an elongate hollow shaft tapering from an opened butt end to a tip end and having a neutral axis of bending located along a center line of the hollow shaft wherein the hollow shaft includes a handle portion located at the butt end for a user to grip;
    an insert disposed along and within the hollow shaft,
    a load member disposed within the hollow shaft along the neutral axis with a first end coupled to the insert; and
    an adjuster assembly coupled between the hollow shaft and a second end portion of the load member for tensioning the load member so as to adjust the bending stiffness of the hollow shaft between the insert and the adjuster assembly, the adjuster assembly being disposed entirely within and spaced a distance inwardly in an axial direction from the butt end of the hollow shaft toward the tip end for facilitating trimming of the butt end of the hollow shaft.

13. The golf shaft assembly of claim 12, further comprising a golf club head mounted on the tip end of the hollow shaft.

14. The golf club assembly of claims 1, 13 or 12, wherein the load member and the hollow shaft are configured to permit the load member to move laterally within the hollow shaft.

* * * * *